United States Patent [19]
Strul

[11] Patent Number: 5,498,261
[45] Date of Patent: Mar. 12, 1996

[54] THERMAL ANGIOPLASTY SYSTEM

[75] Inventor: Bruno Strul, Palo Alto, Calif.

[73] Assignee: Advanced Cardiovascular Systems, Inc., Santa Clara, Calif.

[21] Appl. No.: 811,024

[22] Filed: Dec. 20, 1991

[51] Int. Cl.$^6$ ........................................................ A61B 5/00
[52] U.S. Cl. ........................................................... 606/29
[58] Field of Search ..................... 606/32, 34, 35, 606/27, 28, 31; 128/419 R, 783–786, 804, 399, 401, 403, 908; 219/201, 209, 250, 510–513, 69.19, 85.19; 340/449, 577, 578, 622, 640; 607/96, 98, 99, 103–108, 113, 102

[56] References Cited

U.S. PATENT DOCUMENTS

| | | | |
|---|---|---|---|
| 3,601,126 | 8/1971 | Estes | 606/35 |
| 3,824,374 | 7/1974 | Mayher | 219/510 |
| 4,133,995 | 1/1979 | Buck | 219/510 |
| 4,365,138 | 12/1982 | Hess | 219/201 |
| 4,397,314 | 8/1985 | Vaguine | 128/783 |
| 4,522,194 | 6/1985 | Normann | 128/1 D |
| 4,643,186 | 2/1987 | Rosen et al. | 128/303.1 |
| 4,658,815 | 4/1987 | Farin et al. | 606/34 |
| 4,709,698 | 12/1987 | Johnston et al. | 128/303.12 |
| 4,748,979 | 6/1988 | Hershenson | 128/303.1 |
| 4,754,752 | 7/1988 | Ginsburg et al. | 128/303.12 |
| 4,776,334 | 10/1988 | Prionas | 128/303.1 |
| 4,799,479 | 1/1989 | Spears | 128/303.1 |
| 4,808,164 | 2/1989 | Hess | 604/95 |
| 4,860,744 | 8/1989 | Johnson et al. | 128/303.1 |
| 4,907,589 | 3/1990 | Cosman | 606/34 |
| 4,927,413 | 5/1990 | Hess | 604/95 |
| 4,955,377 | 9/1990 | Lennox et al. | 128/401 |
| 4,967,765 | 11/1990 | Turner et al. | 128/785 |
| 4,969,459 | 11/1990 | Gusakov | 128/399 |
| 4,979,948 | 12/1990 | Geddes et al. | 606/33 |
| 5,019,075 | 5/1991 | Spears et al. | 606/7 |
| 5,035,694 | 7/1991 | Kasprzyk et al. | 606/27 |
| 5,249,585 | 10/1993 | Turner et al. | 607/113 |

*Primary Examiner*—William E. Kamm
*Assistant Examiner*—M. H. Parker
*Attorney, Agent, or Firm*—Fulwider, Patton, Lee & Utecht

[57] ABSTRACT

A system for thermal angioplasty provides electrical power to a heating coil located inside a dilatation balloon, receives a signal from a sensor at the coil indicating its temperature and also receives signals from balloon sensors indicating the temperature at their respective positions. An isolation transformer is used to provide RF power and the sensor signals are optically coupled to provide increased electrical isolation for the patient. The heating coil temperature sensor signal is compared to high and low temperature limits and if either is exceeded, a fault signal is generated. The sensor signals from the balloon are compared to predetermined high temperature limits and if exceeded, fault signals are generated. The current drawn from the battery is compared to a predetermined current level and if exceeded, a fault signal is also generated. Upon generation of any of the fault signals, the electrical power to the heating coil is interrupted by fault detection circuitry. An RF ON reset switch is provided to prevent the inadvertent application of RF power to the heating coil. Materials used in the connectors and in the RF generator for connections to the catheter electrical leads are compatible with those leads to avoid a thermocouple effect.

18 Claims, 11 Drawing Sheets

THERMAL ANGIOPLASTY SYSTEM

BACKGROUND OF THE INVENTION

The invention relates generally to balloon angioplasty for dilating obstructed blood vessels and more particularly, to a system for controlling the heat applied by a dilatation balloon in thermal angioplasty.

In a stenosis caused by plaque creating an obstruction in a vessel wall, a dilatation balloon catheter may be used to enlarge a passage through the stenosis. Typically, the balloon is located at the stenosis and pressurized liquid is passed down the catheter to inflate the balloon, causing it to expand and thereby compress the plaque against the artery walls. Inflation of the balloon results in expansion of the narrowed lumen in the artery, thereby increasing the blood flow after the balloon has been removed. Such outward compression results in stress on the plaque, sometimes causing cracking, tearing and stretching. In some cases, after the balloon catheter is removed, torn plaque and tissue become dislodged from the vessel wall resulting in abrupt reclosure of the vessel. Even when abrupt reclosure does not occur, it is thought that the irregular inner surface of the vessel wall may contribute to restenosis at the same location.

One approach to promote the healing of blood vessels damaged by balloon angioplasty has been the application of heat during the angioplasty procedure. During balloon inflation, the disrupted tissues of the plaque and the arterial wall are heated in order to fuse together fragmented segments of tissue and to coagulate blood trapped within dissected planes of tissue. Upon subsequent balloon deflation, a smooth, cylindrically-shaped channel results.

In one dilatation system where the balloon is filled with liquid for balloon inflation, a heating element, such as a coil, is located on the catheter in the balloon and heats the inflation liquid which transfers the heat to the walls of the balloon by conduction. The balloon in turn transfers the heat to the disrupted plaque and tissues. An electrical power supply provides electrical power to the heating element for the generation of heat. In some prior devices, a radio frequency (RF) generator provides the electrical power to the balloon heating element to generate the heat. A temperature sensing device or devices are located on the heating element and a feedback loop is established with the signal from the sensing device used to control the RF generator to achieve the desired temperature.

In a typical automatic control system, a sensed temperature is compared to the temperature set by the operator and an error signal provided. The error signal is used to automatically regulate the electrical power supply to provide more or less RF energy to the heating coil to obtain the desired temperature. If only a single sensor were used to generate the error signal, inaccuracy of or damage to the sensor may result in over-heating the balloon. If the sensor were to become inaccurate in such a way that the error signal indicated a much lower than actual temperature at the heating element, the RF generator may continue to apply power to the heating element and the balloon may become overheated. Overheating the balloon such that the boiling point is reached and gas and steam are formed in the patient's vessel could have serious effects on the surrounding tissue. Thus, an RF generator which provides multiple automatic controls over the generation of heat would be desirable in a more fail safe system.

Another concern with heat dilatation systems is the inadvertent application of electrical power to the heating element before it is properly positioned at the site to be heated. For example, in the case where the RF generator includes an "RF ON" switch which has been inadvertently left in the "ON" position, and the RF generator is turned on before the dilatation balloon is properly positioned, the heating element may immediately begin to apply heat. Such an inappropriate application of heat may cause injury. Thus, it would be desirable to provide an RF generator having features which would guard against such an inadvertent application of heat.

An additional consideration in thermal dilatation is exposure of the patient to electrical shock. Because the heating coil and the sensors are all used invasively, the patient could be directly exposed to electrical shock in the event that any sensor, or the heating coil itself, is exposed to the patient's bloodstream. For example, should the dilatation balloon burst during the dilatation procedure, the sensors and the heating coil would be exposed to the bloodstream. Although some prior systems include isolation from earth ground, such dilatation systems are sometimes mounted on a metallic pole next to the patient's bed. In the event that exposure of the patient to an invasive electrical lead occurs and a grounding malfunction occurs inside the system, the pole could function as a conductor to earth ground and the patient could experience an electrical shock. Isolation of the patient from exposure to such electrical shocks would be desirable.

A further consideration in the use of sensors to accurately determine a temperature is the thermocouple effect resulting from physically connecting the electrical leads of the sensor to the electrical leads of the electrical power supply when the sets of leads are formed of dissimilar materials. In the case where the materials of the two pairs of electrical leads are incompatible, the physical contact of those leads at a connector can itself generate an electrical current which will vary in dependence on the temperature. This current will add to the electrical current generated by the sensor thus making the electrical current obtained from those leads inaccurate for use in determining the temperature sensed by the sensor.

Hence, those concerned with heat generation and heat control in thermal balloon dilatation systems have long recognized the need for a system which can more quickly and more reliably detect a sensor inaccuracy or other heat control inaccuracy which may lead to over-heating, and which can take appropriate action to protect the patient. It would also be beneficial to provide greater control over the application of electrical power to the heating element to avoid inadvertent applications of heat, as well as to provide a system which lowers the risk of electrical shock to a patient in the event of exposure to the electrical leads of invasive sensors and heating coils. The present invention fulfills these needs.

SUMMARY OF THE INVENTION

Basically, the present invention provides a power generator system having greater control over the heat applied by the heating element of a catheter and greater isolation of a patient from power sources contained in the power generator. In accordance with the principles of the invention, a sensor is provided to sense the temperature of the heating element of the catheter and the output signal of that sensor is monitored for a temperature which falls outside the bounds of predetermined high and low fault temperature thresholds. In the event that the sensed temperature falls outside the range established by the low and high fault temperatures, the electrical power to the heating element is automatically interrupted and an alarm condition is appropriately indicated.

In accordance with another aspect of the invention, multiple temperature sensors disposed at a dilatation balloon are monitored and, if any sensor indicates a temperature exceeding a fault temperature, the electrical power to the heating element is automatically interrupted and an alarm provided.

In accordance with other aspects of the invention, most electrical power sources of the power generator are connected to a generator ground which is isolated from earth ground to lessen the risk of electrical shock to the patient. Further electrical isolation results from the use of an optical isolation system used with the invasive temperature sensors. Signals received from the sensors are converted to optical signals by circuits which are isolated from both earth ground and generator ground. Thus, these sensors and the patient are doubly isolated. The light signal is converted back to an electrical signal by circuits isolated from earth ground.

An isolation transformer is also used to connect the RF electrical power generation circuits to the heating element in the catheter by inductive coupling only. This also isolates the patient from electrical shock.

In another aspect of the invention, a reset switch circuit controls the operation of the electrical power circuit to prevent the inadvertent application of electrical power to the heating element. Upon the interruption of power to the power generator, the reset switch circuit is automatically reset to OFF and the reset switch must be subsequently moved to the ON position before electrical power can be applied to the heating element. This feature lessens the risk that electrical power could be inadvertently applied to the heating element of the catheter before the heating element is properly positioned at the selected site.

In a further aspect in accordance with the invention, the materials used in connecting the electrical leads of the sensors to the power generator are the same as or are compatible with the leads of the sensors. Consequently, physical electrical connections do not act as thermocouples and cause inaccuracy.

Other aspects and advantages of the invention will become apparent from the following detailed description and the accompanying drawings, illustrating, by way of example, the features of the invention.

DETAILED DESCRIPTION OF PREFERRED EMBODIMENTS

Figure 1:
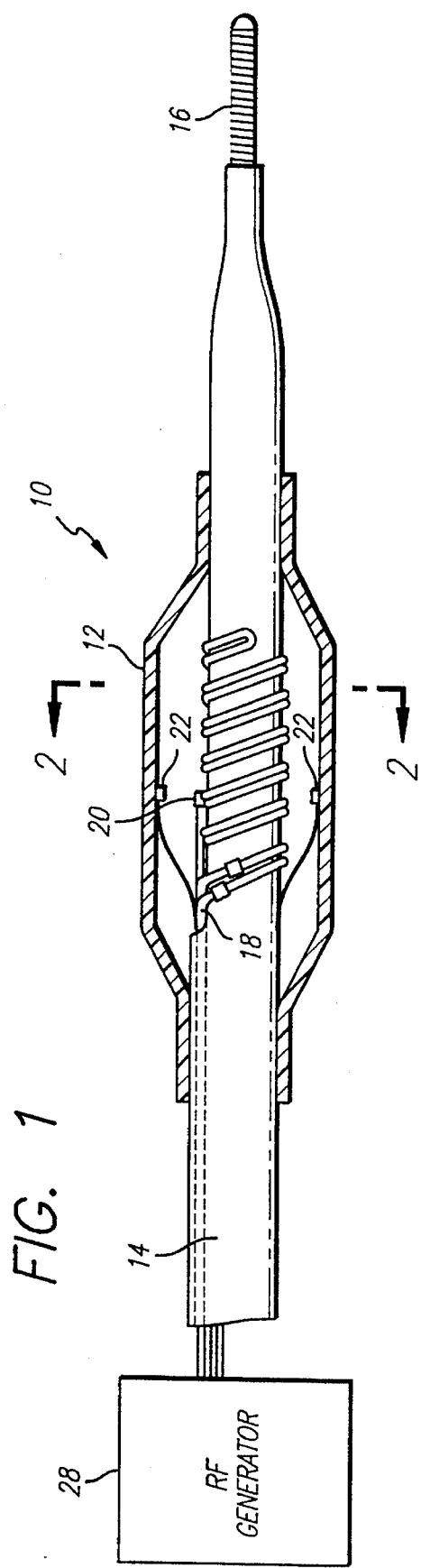
FIG. 1 is a partial cross-sectional view of a thermal balloon dilatation catheter having multiple temperature sensors mounted on the inside surface of the dilatation balloon and a temperature sensor mounted on the heater coil.

Referring now to the drawings with more particularity, wherein like reference numerals designate like or corresponding elements among the several views, there is shown in FIG. 1 a thermal dilatation system 10 having a dilatation balloon 12 mounted on a catheter 14, which may be a perfusion catheter. Shown mounted within the balloon 12 is a heating coil 18. Mounted on the heating coil 18 is a temperature sensor 20, such as a thermocouple. Mounted on the inside surface of the balloon 12 are three temperature sensors 22 which may also be thermocouples. In FIG. 1, only two balloon temperature sensors 22 are shown; however, in FIG. 2, all three sensors 22 are shown and are spaced at approximately 120° intervals around the inside of the balloon 12. Shown protruding from the right side of the catheter in FIG. 1 is a guide wire 16.

Figure 2:
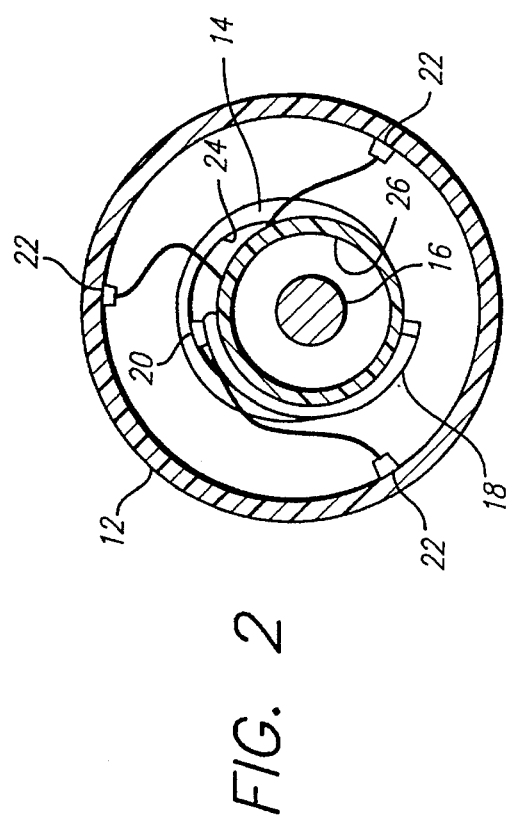
FIG. 2 is a cross-sectional view of the dilatation balloon portion of the catheter of FIG. 1 showing the three balloon temperature sensors and an inflation lumen formed in the catheter.

Referring now to FIG. 2, a cross-sectional view of the catheter 14 at the balloon 12 of FIG. 1 is presented. Contained inside the balloon 12 as part of the catheter 14 is the opening of an inflation lumen 24. As is shown, the electrical leads of the heating coil 18, the electrical leads for the heating coil sensor 20, and the electrical leads of the three balloon temperature sensors 22 are all disposed through the inflation lumen 24. The inflation lumen 24 may also be used to channel the inflation liquid to the balloon for use in inflating and deflating the balloon. Also shown is a guide wire lumen 26 within which the guide wire 16 may be disposed for use in positioning the catheter 14.

Referring again to FIG. 1, the electrical leads of the heating coil 18, the leads of the heating coil temperature sensor 20 and the leads of the balloon temperature sensors 22 are connected to an RF generator 28.

Figure 3:
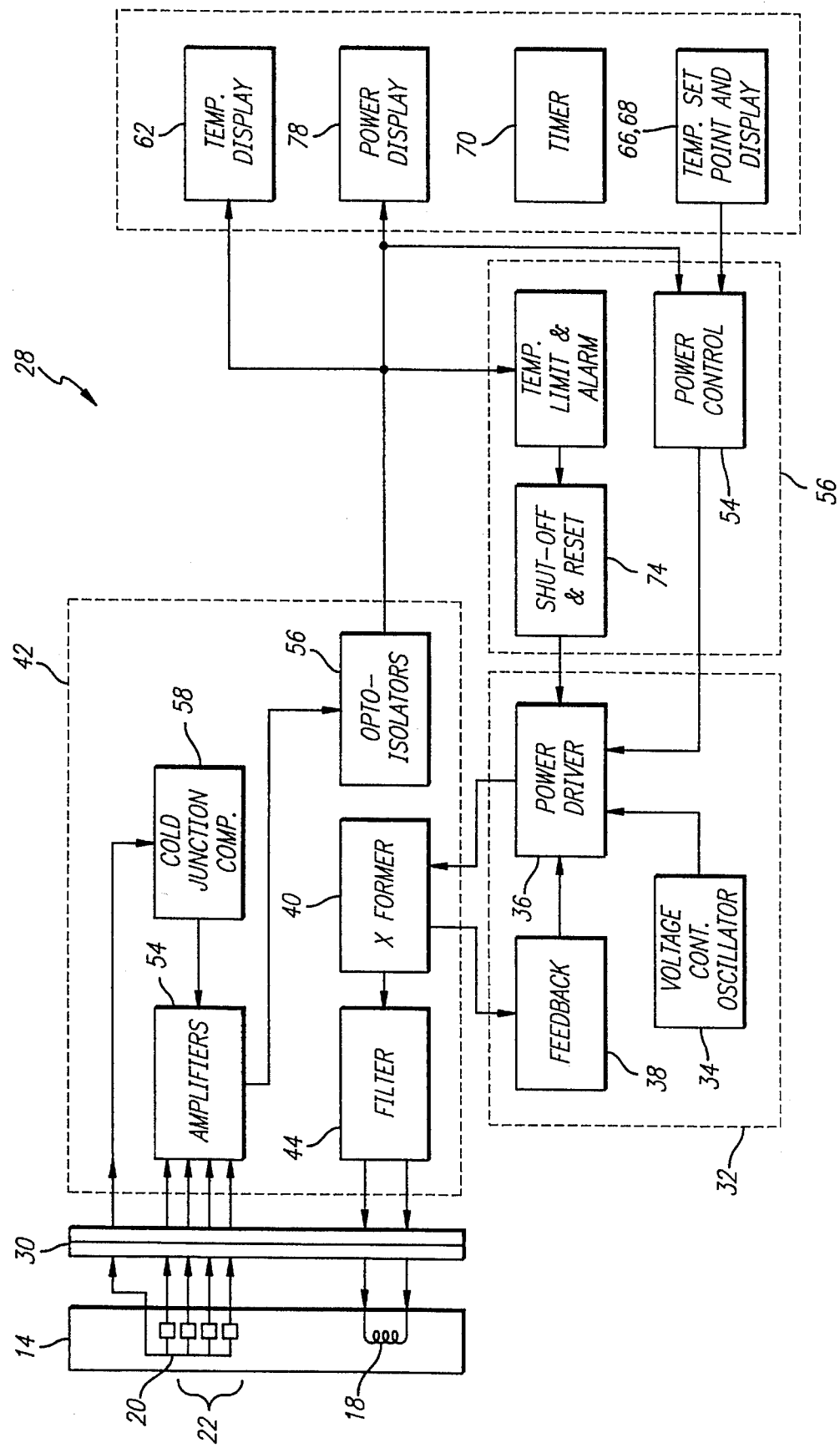
FIG. 3 is a block diagram of a power generator system in accordance with the principles of the invention having an isolation section, an oscillator section, a control section and a display section.

Referring now to FIG. 3, a block diagram of an RF generator 28 in accordance with the principles of the invention is shown. In the embodiment shown in FIG. 3, a pair of connectors 30 are interposed between the electrical leads of the catheter 14 and the electrical leads of the RF generator 28. Although shown as a separate device in FIG. 3, one of the connectors 30 may actually be a part of the RF generator 28. The other connector may be permanently affixed to the electrical leads from the catheter 14. When being readied for use, one connector is plugged into the other. In accordance with an aspect of the invention, the connectors 30 use the same or compatible electrically conductive material as that used for the electrical leads of the catheter 14 and that used for the leads into and out of the RF generator 28. For example, male and female contacts in the plugs and sockets used in the connectors 30 may all be formed of copper which is the same material used for the electrical leads in the catheter and the electrical leads into and out of the RF generator 28. By this feature, physical connections between the leads and the connectors do not act as thermocouples themselves and do not generate signals which may add to the temperature sensor signals thereby causing inaccuracy.

The energy for the heating coil 18 is provided by the oscillator section 32. The oscillator section 32 in this embodiment comprises a voltage controlled oscillator (VCO) 34, a power driver 36 and a feedback circuit 38. The VCO 34 in the preferred embodiment controls the frequency of the power output and provides power at approximately 250 khz although other frequencies may be used. The power driver 36 amplifies the VCO 34 voltage and provides impedance matching to the primary winding of an isolation transformer 40 in the isolation section 42. The transformer 40 selected in the preferred embodiment is a high frequency, step-up power transformer. In the preferred embodiment, an isolation transformer is used; i.e., a transformer providing magnetic coupling between the circuits without introducing significant ohmic coupling or electrostatic coupling between primary and secondary sides. This technique provides increased isolation of the patient's bloodstream from the primary winding, power driver 36 and power supplies of the RF generator. Only inductive coupling exists between the output winding and the primary winding. In one embodiment, the transformer was constructed to provide thirteen watts of output power.

The isolation section 42 also includes a filter 44 coupled to the output of the transformer 40 to remove higher harmonics from the transformer output signal.

In one embodiment, the transformer 40 has a six-turn, center tap primary, a ten-turn secondary for use in stabilization feedback section 38 and a ten-turn secondary for the output. The transformer was constructed from the following electrical components: Clip, transformer assembly, EP20 Core; a core set, ferrite, EP-3c8; bobbin, transformer EP20 Core, PC Mt manufactured by Philips Components; 30 AWG, HML magnet wire and 26 AWG, HML magnet wire manufactured by Belden Co.; and polyimide tape distributed by 3M.

Figure 4:
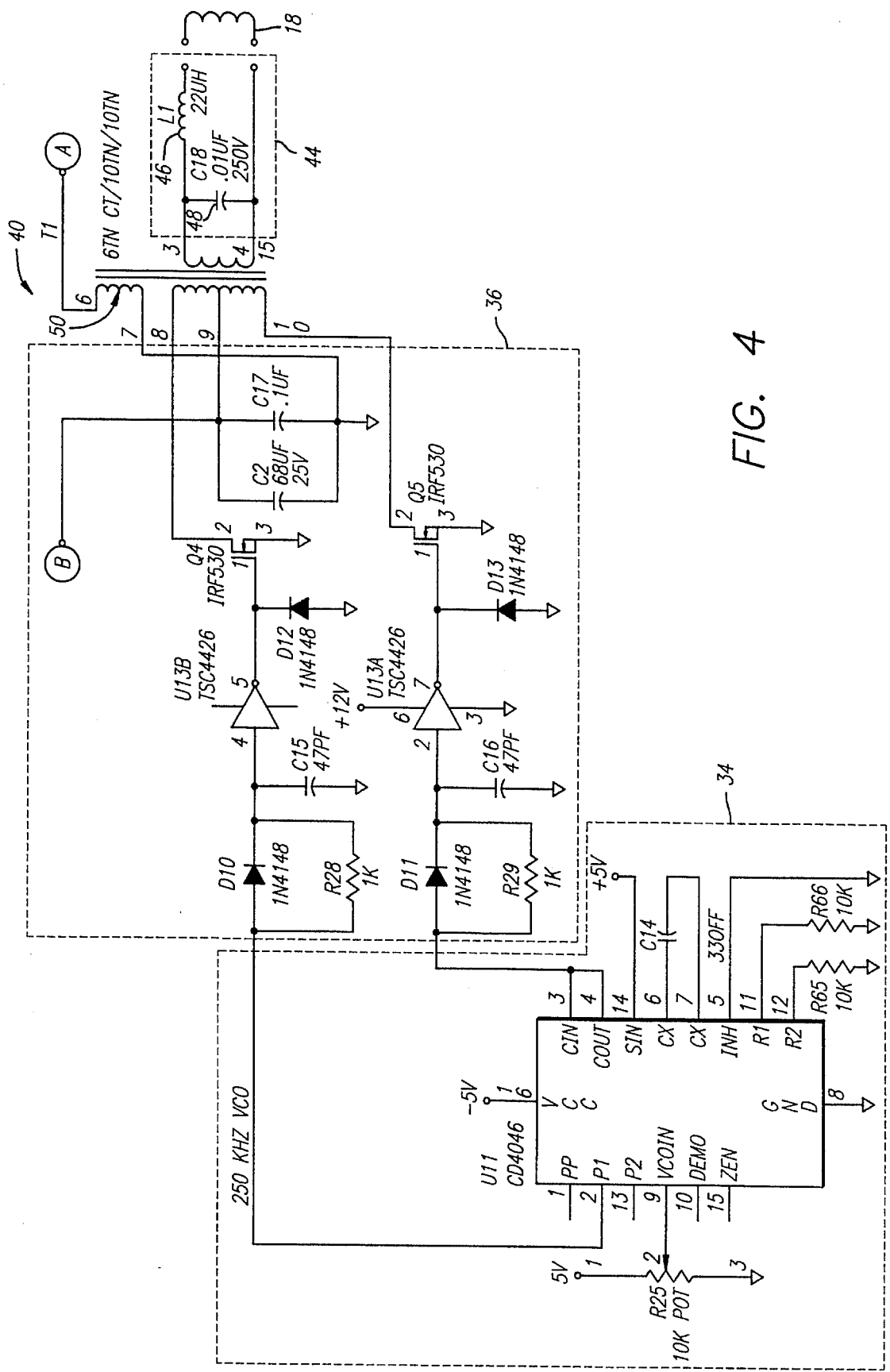
FIG. 4 is an electrical schematic diagram of portions of the oscillator and isolation sections of the system shown in FIG. 3.

Referring now to FIG. 4, schematic diagrams of the VCO 34, power driver 36, transformer 40 and output filter 44 are provided. The VCO 34 has a designation of CD4046, is manufactured by Signetics or Motorola and is set to provide an output signal at 250 khz via potentiometer R25. The 250 khz VCO 34 signal is provided to power FETs Q4 and Q5 which form part of the power driver 36 in this embodiment and are designated by part number IRF530, manufactured by International Rectifier or Motorola. The use of these power FETs results in fast "turn-on" and "turn-off" with relatively little power dissipation. The output signals of the FETs are provided to the primary winding of the transformer 40.

The secondary output winding of the transformer 40 is coupled to the filter 44 shown in this embodiment as a series inductor 46 and parallel capacitor 48. The filter 44 removes higher harmonics from the RF output signal. After the filter 44, the signal is provided to the heating coil 18 to generate heat. In this embodiment the heating coil is a resistive type.

Figure 5A:
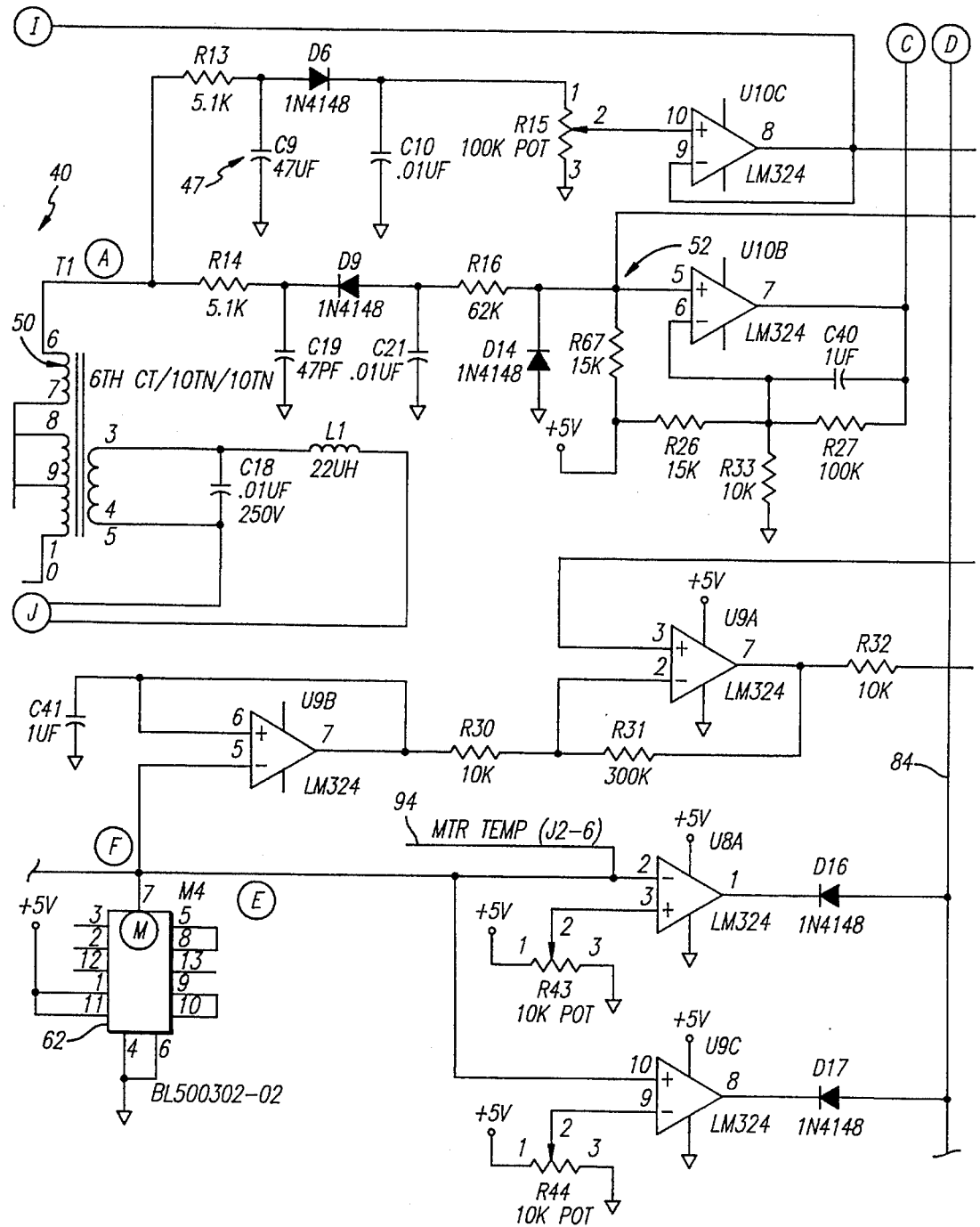
FIG. 5 is an electrical schematic diagram of an isolation transformer, part of a transformer feedback loop, a sensor fault detection circuit and a heating coil temperature monitor and error signal creation circuit.
Figure 5B:
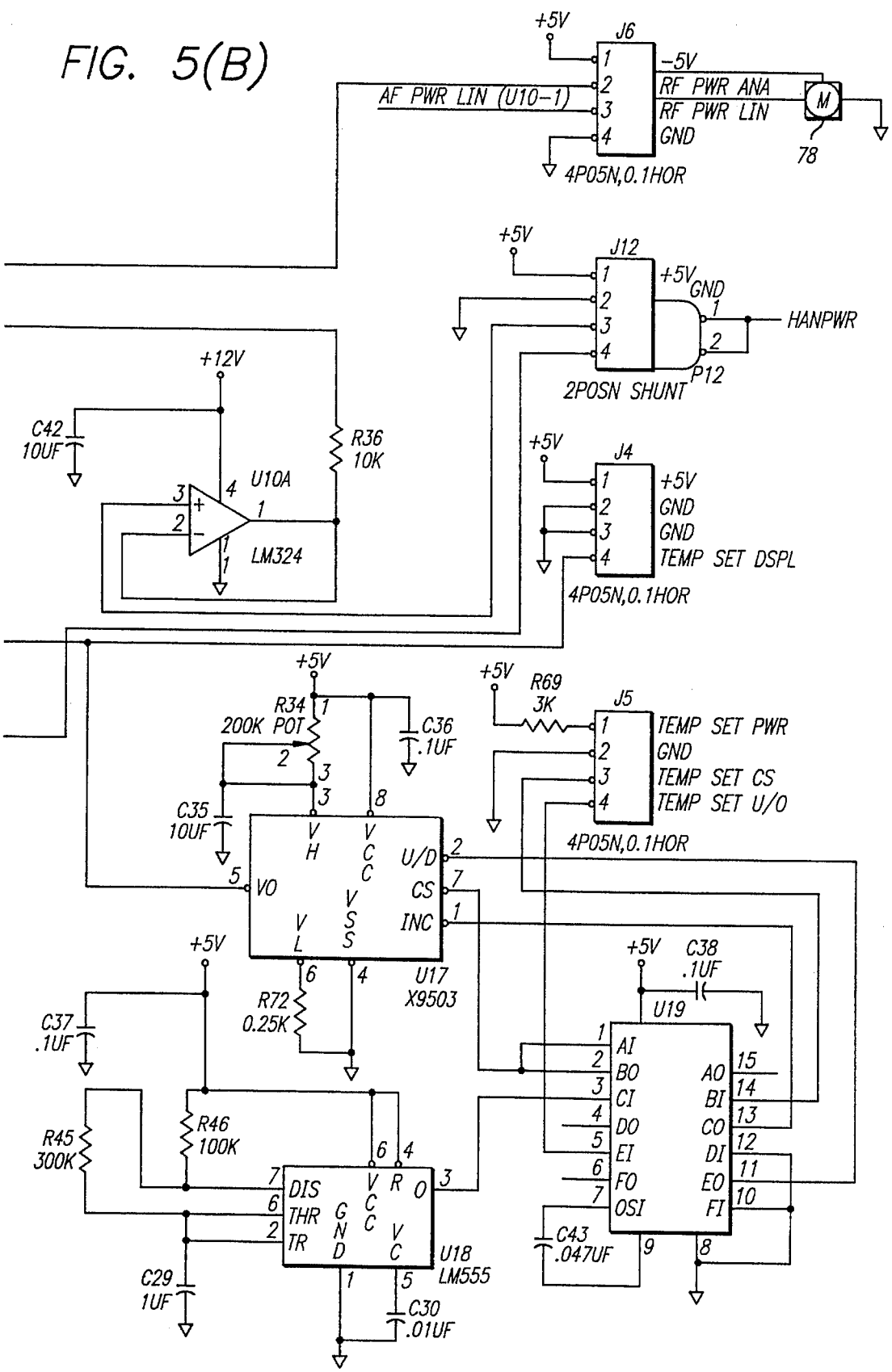
Figure 6:
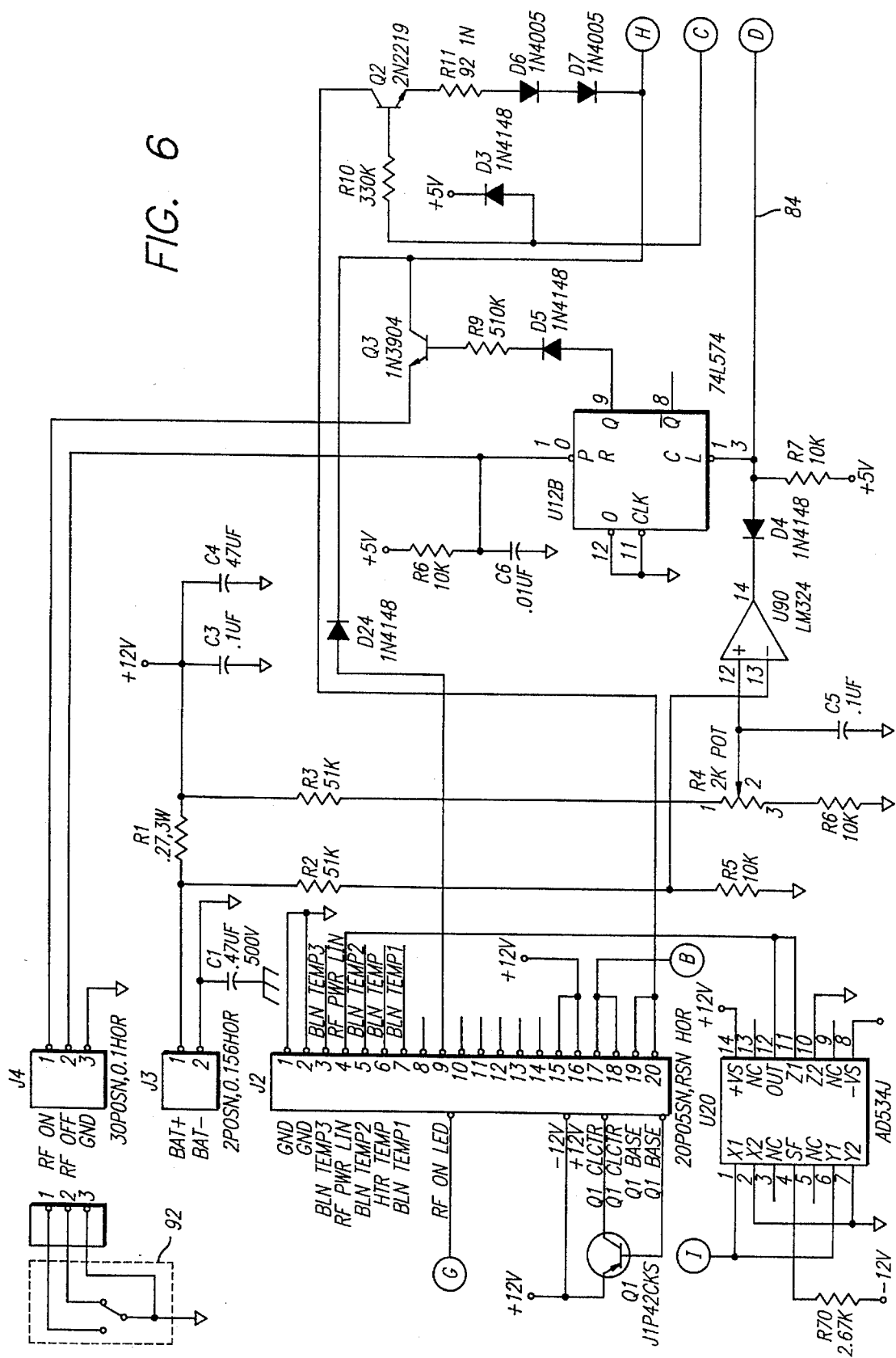
FIG. 6 is an electrical schematic diagram of an RF output control circuit in accordance with the principles of the invention.

The transformer 40 also has an auxiliary primary winding 50 for providing a voltage representative of the transformer 40 output. Referring now to FIG. 5, this voltage is differenced at node 52 with an error voltage which represents the difference between the temperature set for the heating coil 18 and the temperature sensed at the heating coil by the heating coil sensor 20 as will be discussed in detail below. This node difference is provided to a comparator amplifier U10B, which is an LM324 manufactured by National Semiconductor, and the difference signal is used to control the base of transistor Q2 as shown in FIG. 6. The collector of transistor Q2 is coupled to the base of power transistor Q1. The collector of transistor Q1 is connected to the center tap of the primary winding of the transformer 40 (FIG. 4) to control the DC voltage on the center tap of the primary and therefore the RF output from the transformer 40. Thus a stabilization feedback loop from the transformer 40 itself is provided to control the power output. In the event that the error signal indicates a low temperature. Q1 will allow current to flow through the primary winding of the transformer 40 and RF power to be output to the heating coil 18. In the event that the error signal indicates that the heating coil is hotter than the temperature set point, transistor Q1 will be turned off which will stop current from flowing through the primary winding of the transformer 40.

Returning to the isolation section 42 shown in FIG. 3, the inputs from the thermocouples 20 and 22 in the catheter 14 are amplified by respective amplifiers 54 and are then optically coupled by respective optical isolation circuits 56. Respective compensators 58 scale and linearize the thermocouple signals. As will be described below, a doubly isolated power supply is used for the amplifiers 54. Optically coupling the sensor further isolates the patient from the power supplies associated with subsequent signal processing. In the embodiment shown herein, an approximate isolation of two-thousand volts is provided by use of optical coupling.

Figure 7A:
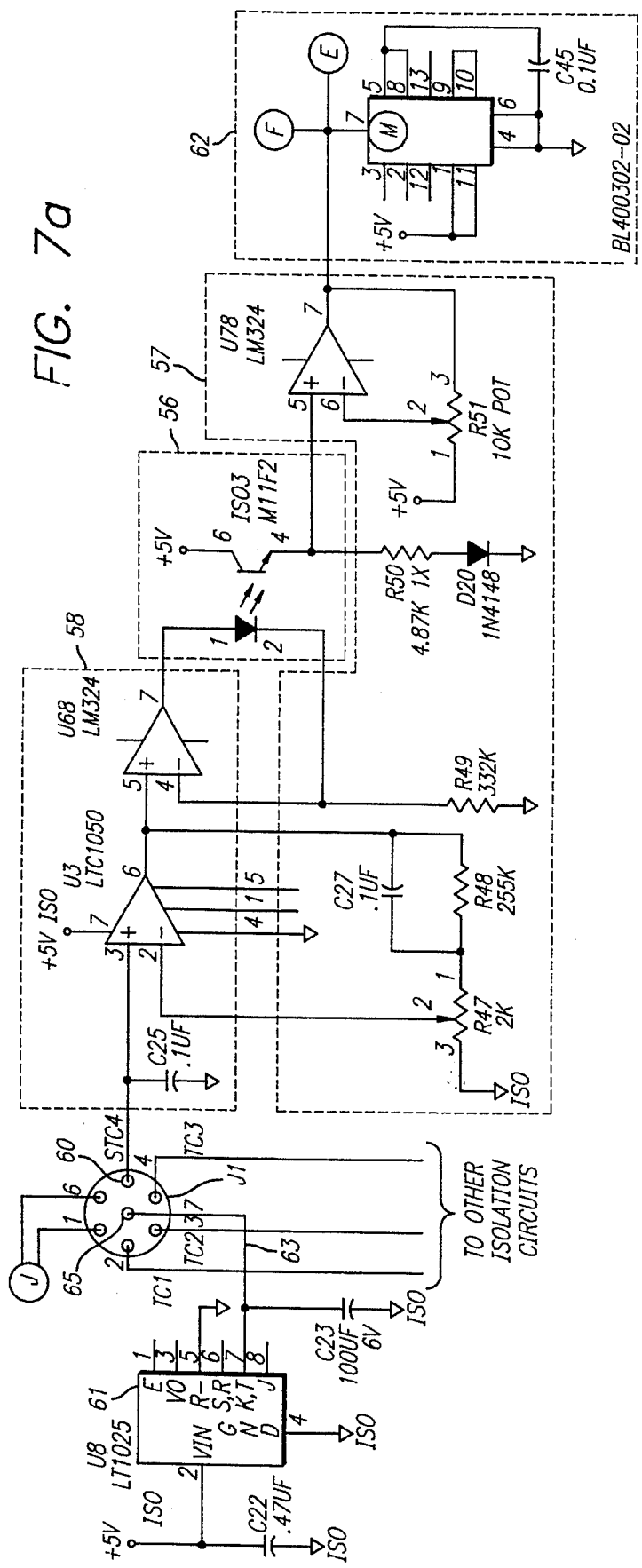
FIGS. 7a and 7b are electrical schematic diagrams of an amplifier circuit for amplifying signals from a catheter sensor, a cold junction compensation circuit, an optical isolation circuit, a display circuit and electrical isolation means.

Also shown in FIG. 7a is a cold junction compensation circuit. A temperature sensitive device 61, in this case an LT1025 device manufactured by Linear Technologies, senses temperature and, in response to the temperature sensed, provides a voltage on its line seven representative of that temperature. In the circuit of FIG. 7a, the output voltage from device 61 representative of the temperature sensed is provided on the common line 63 of the temperature sensors 20 and 22 through the center contact 65 of connector J1. The application of this voltage representative of temperature from device 61 to the common line 63 causes the sensor outputs to represent absolute temperature rather than a relative temperature.

Referring now to FIG. 7a, an embodiment of an optical isolation circuit is presented. The respective sensor signal is received at terminal 60. In this case, the signal from the heating coil sensor 20 will be received at terminal 60. The sensor signal is then applied to amplifier U3, an LTC1050 device manufactured by Linear Technology which linearizes the signal to provide ten millivolts per degree celsius. The linearized signal is then applied through another amplifier U6B, an LM324 device, to the optical coupler 56 which comprises a light emitting diode and a photo-diode which are part of a single device 56 in this embodiment and have a designation of H11F2 manufactured by General Electric. This device converts the linearized electrical signal to an optical signal and then returns it to an electrical signal, thus providing optical isolation. The signal is then scaled and amplified by amplifier U7B, also an LM324 device, and is applied to a display device 62 having a designation of BL400302-02 and manufactured by Modutech. This particular digital display presents four numerals.

Figure 7B:
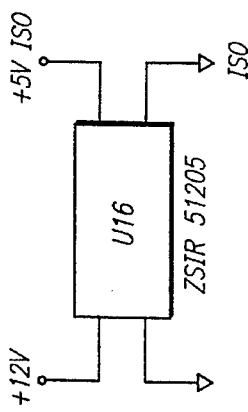

As shown in FIG. 7a, all components prior to the optical coupler, including devices U3 and U6B, have isolated grounds designated in the FIGURE as "ISO." Circuitry in the RF generator has a ground indicated as an upside down equilateral triangle (RF generator ground) to distinguish it from earth ground. As shown in FIG. 6, earth ground is isolated from RF generator ground by capacitor C1. Isolated ground indicated by ISO is not only isolated from earth ground, but is also isolated from RF generator ground. The devices indicated as having ISO ground in FIG. 7a are located on a separate circuit board mounted on insulators inside the RF generator 28. They are powered by a five-volt power supply shown in FIG. 7b which is also isolated from earth ground and from RF generator ground. All of the circuits in the RF generator prior to the optical coupling which receive signals from temperature sensors in the catheter are connected to this ISO ground. These circuits are thus doubly isolated from the patient. Should a balloon burst and a sensor's electrical leads be put into contact with a patient's bloodstream, and should capacitor C1 short to earth ground for any reason, the patient would still be isolated from the pre-optical coupler electrical circuits by this ISO ground. Therefore, the chances of the patient receiving an electrical shock are lessened.

Although only one optical coupler circuit coupled to a single temperature sensor is shown in FIG. 7a, the other temperature sensors 22 each have identical circuits containing their own respective optical couplers, amplifiers and displays. Therefore, there are four such circuits in this embodiment and all are connected to ISO ground and all use the same doubly isolated five-volt power supply as that shown in FIG. 7b.

Figure 8:
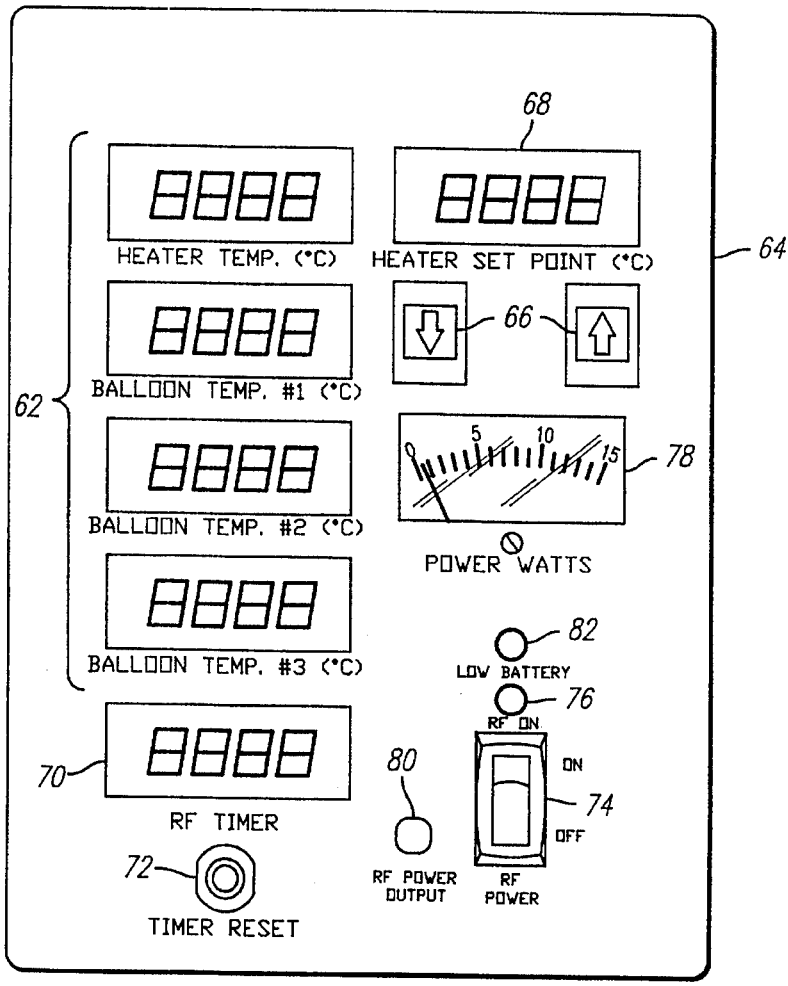
FIG. 8 is an exemplary front panel of an RF generator in accordance with the principles of the invention.

Referring now to FIG. 8, the front panel 64 of an exemplary RF generator 28 is shown. The panel 64 includes four digital temperature displays 62, one for each of the three balloon sensor signals and one for the heating coil temperature. The panel comprises heater set point switches 66 for setting the desired temperature of the heating coil 18 and a heater set point temperature display 68 which informs the operator of the temperature set for the heating coil 18 by the temperature set point switches 66, a timer display 70 of how long RF power has been on, a timer reset switch 72, an RF ON/OFF switch 74, an RF ON indicator 76 (in this embodiment an LED), an analog RF power meter 78, an external connection 80 labeled RF POWER OUTPUT for connecting the RF output to the heating coil of the catheter 14 and for receiving the sensor signals from the catheter 14, and a battery low level indicator 82 (in this case an LED).

Figure 9:
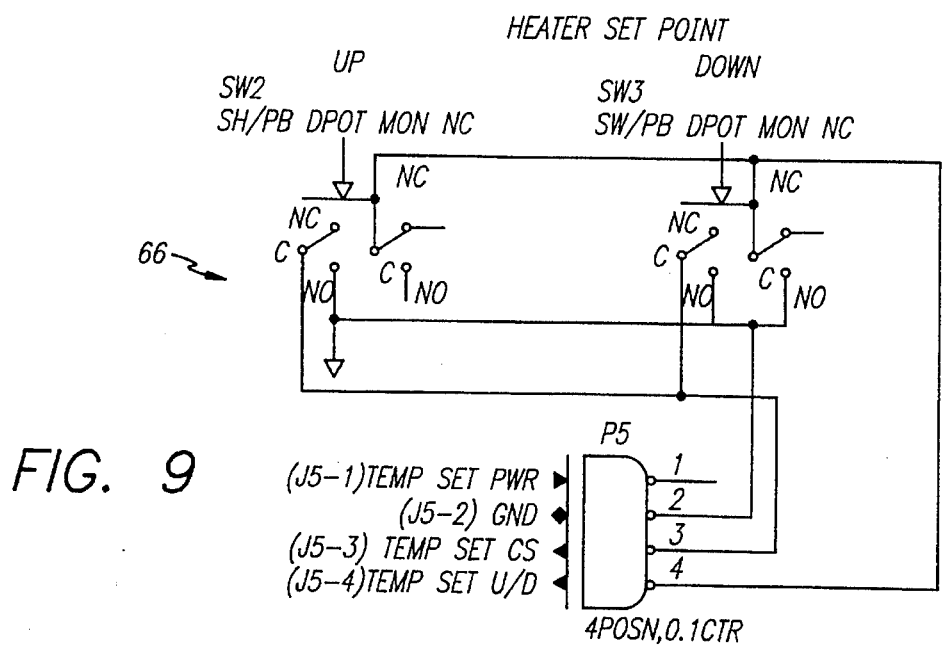
FIG. 9 is an electrical schematic diagram of switches which may be used to set the temperature of the heating coil.

Referring now to FIGS. 9 and 5, the temperature set point may be set by causing contact in the appropriate front panel switch 66. Switches may be the double pole, double throw type switch. The switch contact signals are provided to connector P5 which is connected to connector J5 (FIG. 5) and are provided to U19 which is an MC14490 circuit manufactured by Motorola. Devices U19 provides the temperature set point switch action signals to device U17 which operates as an electronic potentiometer. Device U17 in this embodiment is an X9503 manufactured by Xicor. The temperature set point from device U17 is provided to the temperature set point display connector J4 which provides the signal to the front panel digital indicator 68 as shown in FIG. 8 which may be a BL600302-02 manufactured by Modutech and connected as display 62 is connected as described below. The temperature set point is also provided to device U9A, an LM324 device, which compares it to the temperature sensed by the heating coil sensor 20 to develop an error signal. The error signal is used to control the transformer 40 to provide more or less RF power to the heating coil 18. The error signal is provided first to connector J12 at which a shunt may be inserted as shown. The signal then is provided to device U10A and then to node 52 prior to device U10B for control of the transformer 40 output as described above. Although a shunt is shown at connector J12 in FIG. 5, a fixed voltage may be provided at this point to result in a constant RF power level being provided by the RF generator to the heating coil 18 if desired.

A further feature in accordance with the principles of the invention is a sensor fault detection system. As shown in FIG. 5, the signal representative of the temperature from the heating coil 18 provided to the digital display 62 is also provided to two comparator amplifiers U8A and U9C. Both amplifiers are LM324 devices. The temperature of the heating coil is compared at U8A to a low temperature threshold, for example 10° C. If the signal from the sensor indicates that the temperature sensed is below this low fault temperature, the output of the comparator amplifier U8A will overcome the reverse bias of the in-line diode D16 and provide a fault signal on line 84 to the logic device U12B (FIG. 6) which is a 74LS74 manufactured by Texas Instruments. Upon receiving such a fault signal, the logic device U12B will turn off the base of transistor Q3. Transistor Q3 is connected to the emitter of transistor Q2 and in the event that transistor Q3 is turned off, the emitter of Q2 is opened and transistor Q1 is turned off thereby turning off RF power generation by the transformer 40. In this case, the low fault temperature of 10° C. is below room temperature and should the heating coil sensor 20 indicate such a temperature, failure of that sensor 20 would be indicated. A fault signal would be issued by comparator U8A, RF power to the heating coil 18 interrupted and an alarm provided as described below.

The same general procedure is followed to sense a failure of the automatic control circuitry and the other sensors 22. Referring again to FIG. 5, comparator amplifier U9C compares the heating coil sensor 20 signal from device U7B (FIG. 7a) to a predetermined high fault temperature signal, for example 140° C. If the signal from the sensor 20 indicates a temperature higher than this, the comparator U9C outputs a fault signal through diode D17. This fault signal on line 84 also causes device U12B (FIG. 6) to turn off transistor Q3 thereby turning off power transistor Q1 and interrupting RF power to the heating coil 18.

This latter-described fault system senses both a fault of the automatic temperature control system and a fault of a sensor. In a case where the sensor indicates that the temperature has exceeded the high fault temperature, the error signal circuit may have malfunctioned causing the heating coil to provide too much heat; or a sensor may have malfunctioned. In either case, the RF power is automatically shut off. In the case where a low temperature is indicated by the heating coil sensor, it is concluded that a sensor fault exists because the temperature should not be so low. The RF power is again automatically shut off to avoid overheating.

In the case of the sensors 22 disposed on the inside of the balloon 12 (FIG. 2), the temperature sensed by each sensor is compared to a high fault temperature threshold, for example 100° C., and if exceeded, the RF power is automatically shut off. This over-temperature condition could also be caused by either an automatic temperature control circuit failure or by a sensor fault. In either case, a fault signal from any one of the sensor circuits causes an interruption of RF power to the heating coil 18 and an alarm to be provided. All fault circuits in this embodiment are connected to the same line 84 (FIG. 5) which is connected to the CL port of device U12B (FIG. 6). Thus, a fault condition of any one of the sensors will cause an interruption of RF power and an alarm.

Figure 10:
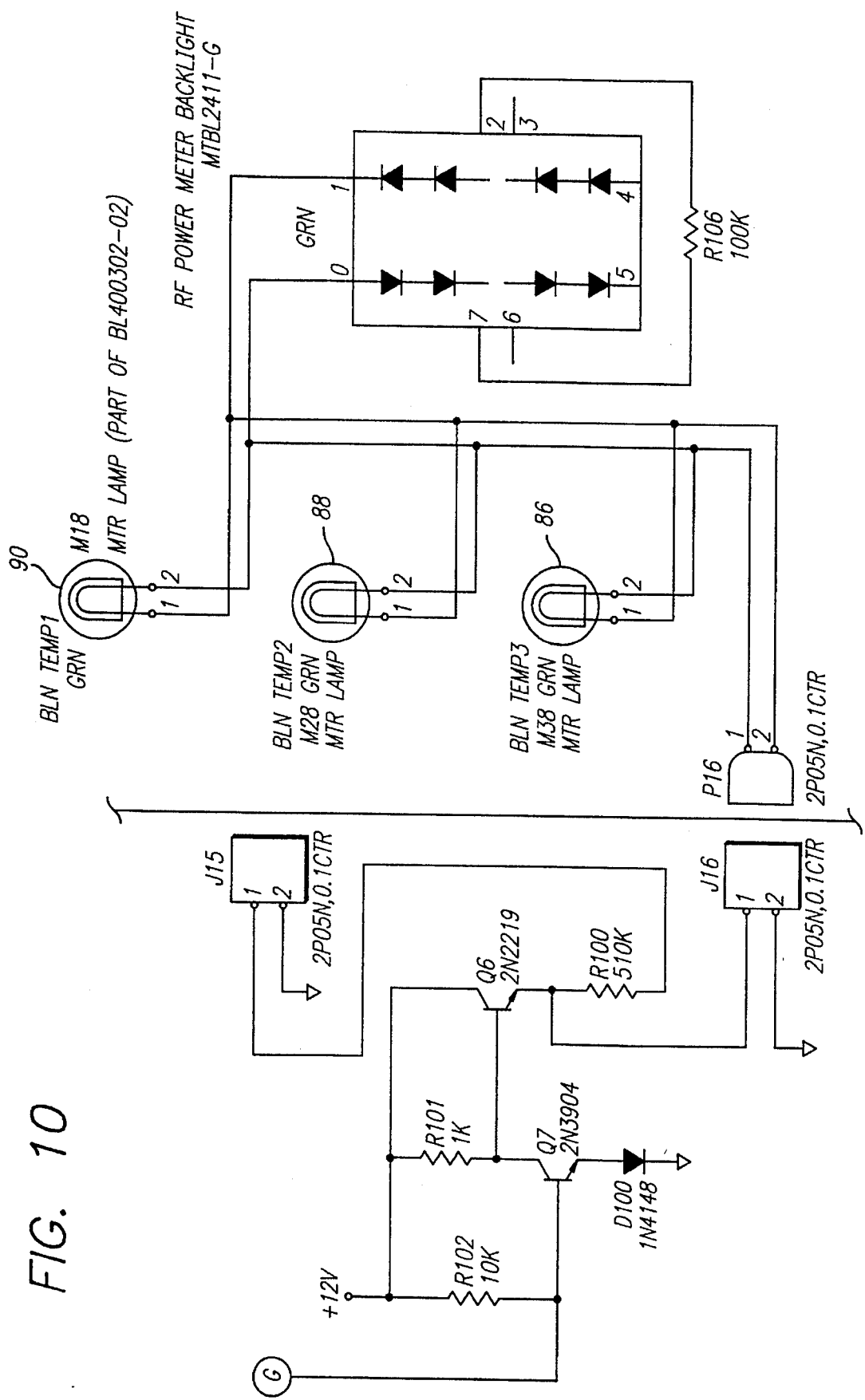
FIG. 10 is an electrical schematic diagram of an alarm circuit in which the background lights of certain temperature displays are turned off.

When transistor Q3 is turned off thereby turning off transistor Q1 and interrupting RF power to the heating coil 18, an alarm is provided. In this embodiment, lights illuminating the digital temperature displays 62 are turned off thus indicating a fault condition. Referring now to FIG. 6, the collector of transistor Q3 is connected to connector J2, pin nine. Referring now to FIG. 10, this pin nine is connected to the base of transistor Q7. Transistor Q7 controls the power to the background lights 86, 88, and 90 for the temperature displays of the three balloon sensors 22. Should transistor Q3 be turned off, these lights would extinguish leaving the temperature displays of these sensors dark. Other alarms may be provided as desired.

In accordance with a further aspect, a system is included which monitors the current drawn from the battery and automatically interrupts the RF power to the heating coil 18 and provides an alarm if that current exceeds a predetermined level, for example four amperes. Referring now to FIG. 6, connector J3 is connected to the battery. Comparator amplifier U9D compares at its negative input port a signal derived from the battery current to a signal at its positive input port representative of a predetermined current level. When the battery current exceeds the setpoint, a fault signal is placed on line 84 and is received by device U12B as are the other fault signals resulting from sensor signals. Device U12B then causes an interruption in RF power and an alarm as described above.

Another aspect is the prevention of the application RF power to the heating coil 18 unless the RF ON/OFF reset switch 92 has been moved first to the RF OFF position after the application of power to the RF generator 28 and then to the RF ON position. This movement is required even if the switch is already in the RF ON position when power to the RF generator is applied. In one embodiment, a single pole, double throw switch 92 is connected at connector J9 (FIG. 6). The RF OFF position of the switch 92 is connected to port PR of device U12B. As described previously, device U12B controls the base of transistor Q3 which controls the base of power transistor Q1 and thus the application of RF power to the heating coil 18.

As shown in FIG. 6, device U12B requires that the RF ON/OFF switch 92 be reset to the RF OFF position before device U12B will allow power to be applied to the base of transistor Q3. Upon the initial application of power to the RF generator 28, device U12B is powered and is held to a high level by the five-volt supply through resistor R8. However, device U12B will not permit the application of voltage to the base of transistor Q3 unless device U12B is reset (grounded) by movement of the RF ON/OFF switch 92 to the RF OFF position. When the RF ON/OFF switch 92 is then moved to the RF ON position, transistor Q3 will be turned on thereby turning on transistor Q1 and RF power output.

The embodiment shown in FIGS. 5 and 6 also provide outputs to recorder devices. Referring to FIG. 5, a recorder signal line 94 is connected prior to the input to comparator amplifier U8A. This recorder line 94 is made available at connector J2 as shown in FIG. 6 at pin six in this case. Recorder outputs are made available for all three balloon temperature sensors (connector J2 pins three, five and seven), the heating coil temperature sensor (connector J2 pin six) and the output of the isolation transformer 40 (connector J2 pin four). As shown in FIGS. 5 and 6, the output of the auxiliary primary winding 50 of isolation transformer 40 is rectified, filtered and connected through buffer amplifier U10C to pin four of connector J2 in FIG. 6 to make the signal available for recording.

Figure 11:
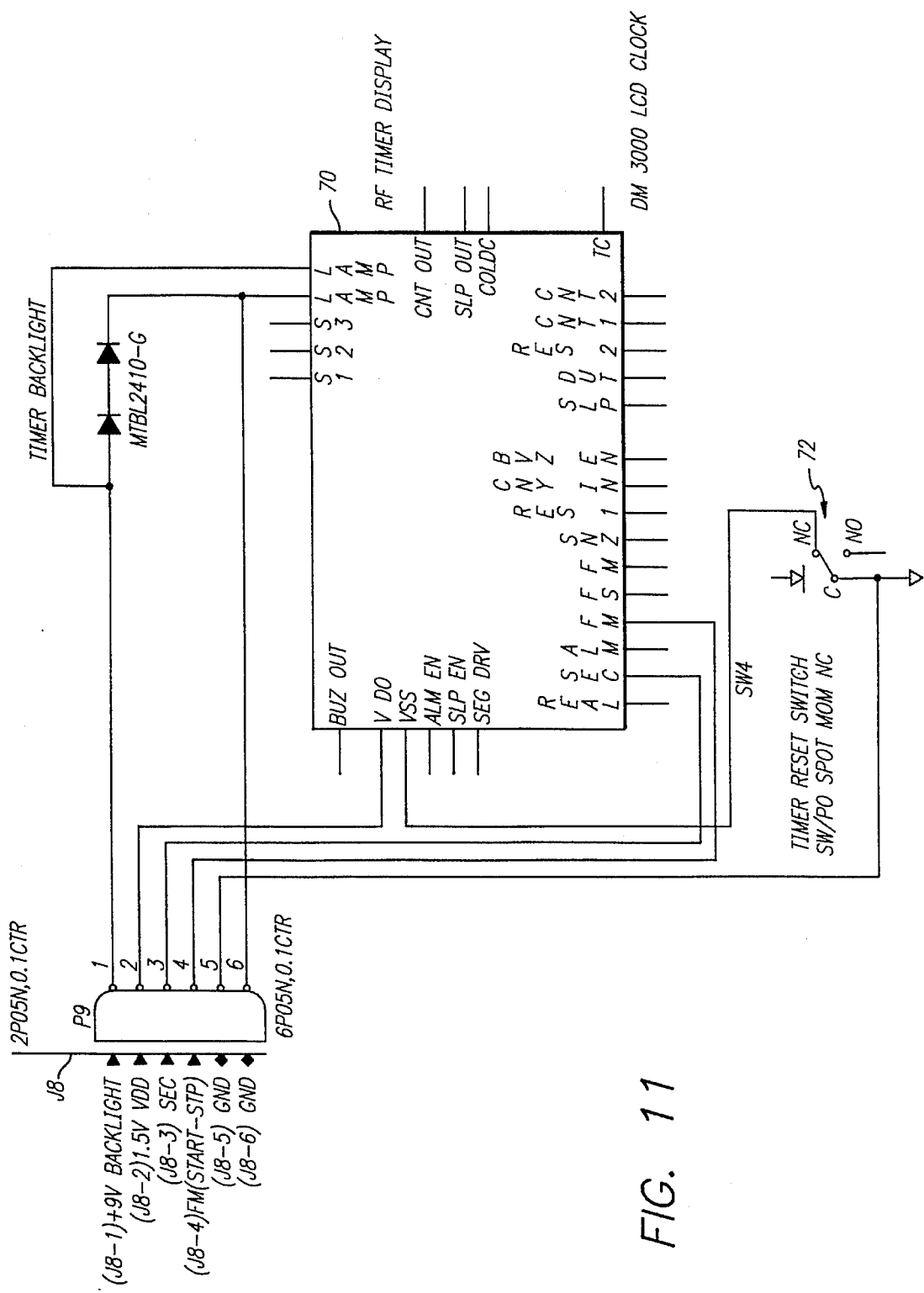
FIG. 11 is an electrical schematic diagram of part of an RF timer circuit.
Figure 12:
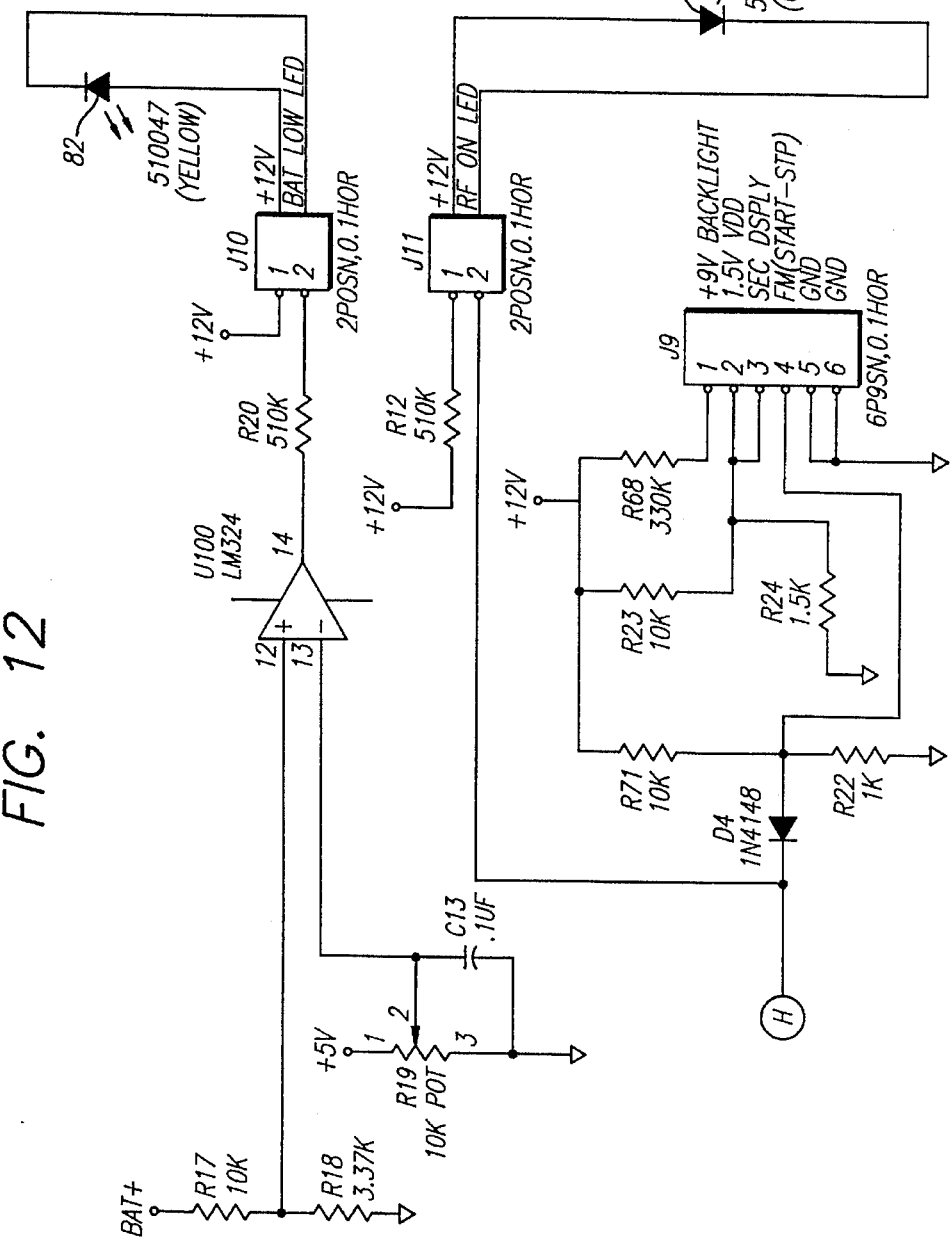
FIG. 12 is an electrical schematic diagram of part of the RF timer circuit and a battery low level indication circuit.

Referring now to FIG. 11, the timer 70 used is a DM 3000 LCD clock manufactured by DigiMeter and is connected through connector P8 to connector J8 shown in FIG. 12. The timer 70 displays the elapsed time that the RF power has been applied to the heating coil 18. The time may be reset to start again by pressing the timer reset button 72 (FIG. 8 also).

Referring again to FIG. 12, a battery low level circuit is shown which provides a signal to connector J10 that the battery voltage has decreased below a predetermined level. Comparator amplifier U10D compares the voltage-divided battery voltage to a level set by potentiometer R19. Should the divided battery voltage decrease beyond the predetermined level, the yellow-colored LED 82 (FIG. 8) will illuminate. The LED in this embodiment is a 51007H7.

Also shown in FIG. 12 is the RF ON light 76 circuit. The collector of transistor Q3 is coupled to the LED 76 which is a 5100HS and is green in color.

Figure 13:
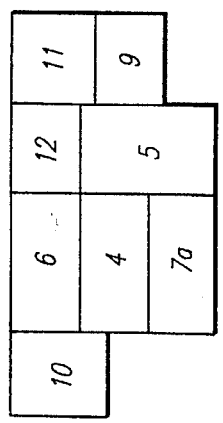
FIG. 13 is a layout of the FIGURES having circuit schematics.

Referring now to FIG. 13, a layout of the FIGURES containing circuit schematics is presented to show how the various FIGURES may be coupled together.

Although shown in the form of a coil mounted on the catheter, the heating element may take other forms. For example, it may take the form of a conductive layer on the interior of the dilatation balloon, such as that disclosed in U.S. Pat. No. 5,035,694 to Kasprzyk et al. or the wire meshwork in the outside wall of the balloon as disclosed in U.S. Pat. No. 4,799,479 to Spears.

As used herein, the word "exceed" when coupled with temperature limits means to go beyond the limits of, whether that limit be a high temperature or a low temperature. In the case of a low temperature limit, to "exceed" that low temperature limit would be to provide a temperature lower than that limit temperature.

Although specific embodiments of the invention have been described and illustrated it is clear that the invention is susceptible to numerous modifications and embodiments within the ability of those skilled in the art, and without the exercise of the inventive faculty. Thus, it should be understood that various changes in form, detail and application of the present invention may be made without departing from the spirit and scope of the invention.

What is claimed is:

1. A power generator for providing electrical power to a heating element of a catheter, the heating element having a temperature, the power generator comprising:

a temperature sensor for providing a temperature signal representative of the temperature at the heating element;

comparator means for comparing the temperature signal to signals representative of a predetermined temperature range and for providing a fault signal when the temperature signal indicates a temperature outside the range;

power source means for providing power to the heating element and for interrupting the power to the heating element in response to the fault signal;

alarm generator means for providing an alarm in response to the fault signal;

first isolation means for providing a first ground in the power generator for electrically interconnecting components of the power generator and for isolating the first ground from earth ground; and second isolation means for isolating the temperature signal from both the first ground and earth ground.

2. The power generator of claim 1 wherein the second isolation means includes an optical coupler which converts the temperature signal from the sensor into an optical signal.

3. The power generator of claim 2 wherein the second isolation means includes an isolation transformer which couples the power from the power source means to the heating element by inductive coupling.

4. A power generator for providing electrical power to a heating element of a catheter, the heating element having a temperature, the power generator comprising:

a temperature sensor for providing a temperature signal representative of the temperature at the heating element;

comparator means for comparing the temperature signal to signals representative of a predetermined temperature range and for providing a first fault signal when the temperature signal indicates a temperature outside the range;

a manually resettable power source means for providing power to the heating element and for interrupting the power to the heating element in response to a fault signal until a manual reset of the power source means has occurred;

the power source means including a battery which provides current to the heating element;

a battery current comparator means for comparing the current from the battery to a predetermined threshold current level and for providing a second fault signal if the predetermined current threshold level is exceeded;

wherein the power source means is responsive to both the first and the second fault signals to interrupt electrical power to the heating element; and alarm generator means for providing an alarm in response to both the first and the second fault signals.

5. A power generator for providing power to a heating element of a catheter which has a dilatation balloon, the heating element having a temperature, the power generator comprising:

a first temperature sensor for providing a first sensor signal representative of the temperature at the heating element;

a second temperature sensor for providing a second sensor signal representative of the temperature at the balloon;

first comparator means for comparing the first sensor signal to a first threshold signal representative of a first predetermined fault temperature and for providing a first fault signal when the first sensor signal indicates a temperature which is less than the first fault temperature;

second comparator means for comparing the second sensor signal to a second threshold signal representative of a second predetermined fault temperature and for providing a second fault signal when the second sensor signal indicates a temperature which exceeds the second fault temperature;

a manually resettable power source means for providing power to the heating element and for interrupting power to the heating element in response to the first or second fault signal until after a manual reset of the power source means has occurred; and an alarm generator means for providing an alarm in response to the first or second fault signal.

6. The power generator of claim 5 further comprising third comparator means for comparing the first sensor signal to a third threshold signal representative of a third predetermined fault temperature and for providing a third fault signal when the first sensor signal indicates a temperature which is greater than the third fault temperature.

7. The power generator of claim 6 wherein the third predetermined fault temperature is below room temperature.

8. The power generator of claim 5 further comprising a heating element reset switch means for controlling the power source means such that the reset switch means must be moved to an on position before the power source means will supply power to the heating element and for automatically resetting to an off position when power to the power generator has been interrupted.

9. The power generator of claim 5 wherein:

the power source means comprises a battery which provides current to the heating element and a battery current comparator means for comparing the current from the battery to a predetermined threshold current level and for providing a third fault signal if the predetermined current level is exceeded;

wherein the power source means is responsive to the first, second or third fault signals to interrupt the power to the heating element; and wherein the alarm generator means is responsive to the first, second and third fault signals to provide an alarm.

10. The power generator of claim 5 wherein:

the temperature sensors include electrically conductive leads formed of a material; and a connector receives the electrically conductive leads of the temperature sensors;

wherein the portions of the connector which make contact with the electrically conductive leads of the temperature sensors are formed of a material which is the same as, or is compatible with, the material of the electrically conductive leads of the temperature sensors.

11. A power generator for providing power to a heating element of a catheter which has a dilatation balloon, the heating element having a temperature, the power generator comprising:

a first temperature sensor for providing a first sensor signal representative of the temperature at the heating element;

a second temperature sensor for providing a second sensor signal representative of the temperature at the balloon;

first comparator means for comparing the first sensor signal to a first threshold signal representative of a first predetermined fault temperature and for providing a first fault signal when the first sensor signal indicates a temperature which is lower than the first fault temperature;

second comparator means for comparing the second sensor signal to a second threshold signal representative of a second predetermined fault temperature and for providing a second fault signal when the second sensor signal indicates a temperature which exceeds the second fault temperature;

power source means for providing power to the heating element and for interrupting power to the heating element in response to the first or second fault signal;

an alarm generator means for providing an alarm in response to the first or second fault signal;

first isolation means for providing a first ground in the power generator for electrically interconnecting components of the power generator and for isolating the first ground from earth ground; and second isolation means for isolating the power provided to the heating element from both the first ground and earth ground and for isolating the signal received from the first and second sensors from both the first ground and earth ground.

12. The power generator of claim 11 wherein the second isolation means includes an optical coupler which converts the first and second sensor signals into optical signals.

13. The power generator of claim 12 wherein the second isolation means includes an isolation transformer which couples the power from the power source means to the heating element by inductive coupling.

14. A power generator for providing electrical power to a heating element of a catheter which includes a dilatation balloon, the heating element having a temperature, the power generator comprising:

a first temperature sensor for providing a first sensor signal representative of the temperature at the heating element;

a second temperature sensor for providing a second sensor signal representative of the temperature at the balloon;

first comparator means for comparing the first sensor signal to a first threshold signal representative of a first predetermined low fault temperature and for providing a first fault signal when the first sensor signal indicates a temperature which is lower than the first fault temperature;

second comparator means for comparing the first sensor signal to a second threshold signal representative of a predetermined high fault temperature and for providing a second fault signal when the first sensor signal indicates a temperature higher than said second fault temperature;

third comparator means for comparing the second sensor signal to a third threshold signal representative of a third predetermined fault temperature and for providing a third fault signal when the second sensor signal indicates a temperature greater than the third fault temperature;

power source means for providing power to the heating element and for automatically interrupting power to the heating element in response to the first, second or third fault signal;

first isolation means for providing a first ground in the power generator and for isolating the first ground from earth ground;

second isolation means for isolating the signal from the first and second sensors from both the first ground and earth ground;

the second isolation means includes an optical coupler which converts the signals from the first and second sensors into optical signals for provision to the first, second, and third comparator means; and an alarm generator means for providing an alarm in response to the first, second or third fault signal.

15. The power generator of claim 14 further comprising heating element reset switch means comprising an on position and off position for controlling the operation of the power source means such that the reset switch means must be moved to said on position before the power source means will supply power to the heating element and for automatically resetting to said off position when power to the power generator has been interrupted.

16. The power generator of claim 14 wherein the second isolation means further comprises:

an isolation transformer which couples the power from the power source means to the heating element by inductive coupling.

17. The power source means of claim 14 wherein the power source means includes a battery which provides current to the heating element and a battery current comparator means for comparing the current from the battery to a predetermined threshold current level and for providing a fourth fault signal if the predetermined current level is exceeded;

wherein the power source means is responsive to the first, second, third and fourth fault signals to interrupt the power to the heating element; and wherein the alarm generator means is responsive to the first, second, third or fourth fault signals to provide an alarm.

18. The power generator of claim 14 wherein the temperature sensors include electrically conductive leads formed of a material and the power generator further comprises:

a connector which receives the electrical leads of the sensors;

wherein the portions of the connector which make contact with the leads of the sensors are formed of a material which is the same as, or is compatible with, the material of the electrical leads of the sensors.

* * * * *